United States Patent [19]

Epstein et al.

[11] 4,435,828
[45] Mar. 6, 1984

[54] FLUORESCENCE LASER EXAFS

[75] Inventors: Harold M. Epstein; Robert E. Schwerzel, both of Columbus; Paul G. Andrus, Powell, all of Ohio

[73] Assignee: Battelle Development Corporation, Columbus, Ohio

[21] Appl. No.: 368,256

[22] Filed: Apr. 14, 1982

[51] Int. Cl.³ .............................................. G01N 23/22
[52] U.S. Cl. ...................................... 378/49; 378/149
[58] Field of Search ...................... 378/45, 46, 47, 48, 378/49

[56] References Cited

U.S. PATENT DOCUMENTS

| 3,663,812 | 5/1972 | Koenig | 378/49 |
| 4,169,228 | 9/1979 | Briska | 378/45 |
| 4,317,994 | 3/1982 | Mallozzi | 378/53 |

Primary Examiner—Craig E. Church
Attorney, Agent, or Firm—Philip J. Pollick; Philip M. Dunson

[57] ABSTRACT

Apparatus (10) for obtaining fluorescence laser EXAFS (Extended X-ray Absorption Fine Structure). A lens (12) directs a pulse of radiant energy (13) onto a metal target (15) to produce X-rays (16). A baffle (17) directs the X-rays (16) onto a spectral-dispersive monochromator (18) which directs the spectrally-resolved X-rays (16R) therefrom onto a sample (11). Fluorescence X-rays (27) from the sample (11) strike a phosphor (26) on a grid (19). Emitted light (21) from the phosphor (26) corresponds spatially to the spectral resolution of the X-rays (16R). Emitted light intensity at a point along the spatial distribution corresponds to the absorption characteristics of the sample (11) at a particular wavelength of the incoming X-rays (16R). An imaging lens (20) directs the emitted light (21) onto photographic film or an array detector (22). A reference spectrum of the spectrally-resolved X-rays (16R) is obtained by placing photographic film or an array detector (29) in the path of the spectrally-resolved X-rays (16R) so that only a portion of the X-rays (16R) throughout the spectrum strikes the film or array detector with the remaining portion throughout the spectrum allowed to pass to the sample (11).

28 Claims, 3 Drawing Figures

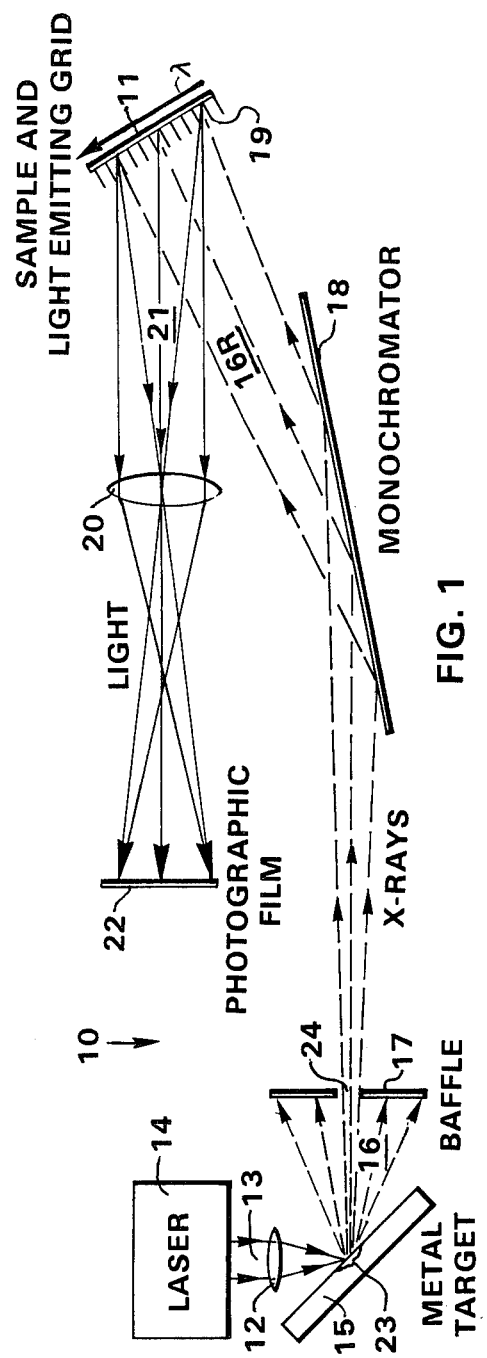
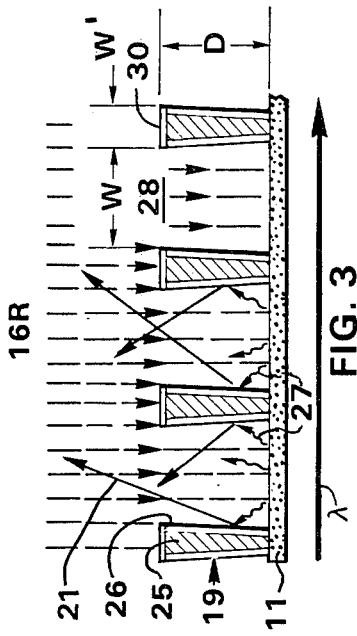
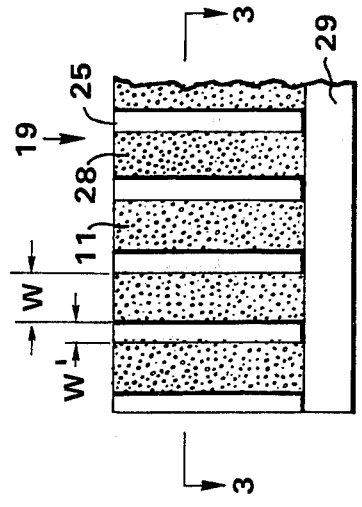
FIG. 1
FIG. 2
FIG. 3

FLUORESCENCE LASER EXAFS

FIELD

This invention relates to Extended X-ray Absorption Fine Structure (EXAFS) spectroscopy. More specifically, it relates to EXAFS spectroscopy using laser-produced X-rays and a fluorescence X-ray detection system.

BACKGROUND

As described in U.S. Pat. No. 4,317,994 (Mallozzi, et al., Mar. 2, 1982), the development of laser-plasmas as an X-ray source for EXAFS has made possible a wide variety of significant experiments that were previously impossible or impractical. However, many of these experiments involve organometallic compounds in which the component of interest is in very low concentration, i.e., iron in blood or magnesium in chlorophyll. In addition, studies on may organic compounds with low concentrations of phosphorus, sulfur, chlorine, potassium, and calcium are of interest. One problem with these low concentration experiments is the poor spectral resolution due to the low signal to background noise ratio. Another difficulty with EXAFS experiments is the necessity for preparing very smooth and very thin samples. These sample requirements often rule out the EXAFS technique for routine laboratory or industrial applications.

Both of these problems can be overcome by using a fluorescence X-ray detection system. Such a detection system has been estimated to enable EXAFS experiments on samples as dilute as 0.01 ppm (Sparks, C. J., "Research with X-rays" *Physics Today*, 1981, 34(5), pp. 40-47.). This detection system also allows for the use of a wide variety of sample states such as solids, powders, and liquids and obviates the need to prepare the very smooth and thin samples required with conventional EXAFS techniques. As a result, this technique is much more amenable to routine laboratory and industrial applications.

SUMMARY OF THE INVENTION

Typical apparatus according to the present invention for obtaining EXAFS data of a material comprises means for directing radiant energy from a laser onto a target to produce X-rays of a selected spectrum and intensity at the target, means for directing X-rays from the target onto spectral-dispersive means so located as to direct the spectrally-resolved X-rays onto a sample of material, means for absorbing the fluorescence X-rays emitted from the sample so that the absorbing means emits light that is spatially resolved so as to correspond to the energy of the spectrally-resolved X-rays striking the sample and whose intensity at any point along the spatial distribution corresponds to the intensity of the fluorescence X-rays produced by a particular energy of incoming spectrally-resolved X-rays, means for directing the emitted light onto recording means, and means for obtaining a reference spectrum of the spectrally-resolved X-rays.

Typically the fluorescence X-ray absorbing means comprises an array of elements arranged to permit incoming X-rays to pass between the elements and enter the sample and be absorbed thereby. The fluorescence X-ray absorbing means then absorbs the fluorescence X-rays emitted by the sample and emits light whose spatial distribution corresponds to the spectral distribution of the incoming X-rays and whose intensity corresponds to the X-ray absorption characteristics of the sample at a particular energy of the incoming X-rays. Preferably the fluorescence X-ray absorbing means is of such design so as to minimize the absorption of incoming X-rays and maximize the absorption of fluorescence X-rays.

Typically the spatially resolved light emitted from the fluorescence X-ray absorbing means is passed through a lens which images the light onto an array detector or photographic film. Preferably the fluorescence X-ray absorbing means comprises light-emitting material which has a decay time and optical-spectra peak which corresponds to the response time and optimal sensitivity of the recording means. Typically the recording means may be photographic film or an array detector.

Typically a reference spectrum of the incoming X-rays is obtained by placing both the recording means and sample in the path of the incoming X-rays so as to enable the recording of both the spectrally-resolved X-ray reference spectrum and the light spectrum of the sample with one laser burst. Alternatively, the light spectrum of the sample and the spectrally-resolved X-ray reference spectrum can be recorded by using separate laser bursts.

Unwanted radiation arising from diluents of the studied material can be removed advantageously by the use of suitable filters between the sample and the fluorescence absorbing means.

DRAWINGS

FIG. 1 is a schematic top view of a typical fluorescence laser-EXAFS apparatus according to the present invention.

FIG. 2 is a front view of the fluorescence X-ray absorbing means, sample, and reference spectrum detection means of FIG. 1.

FIG. 3 is a top sectional view of the fluorescence X-ray absorbing means taken in the plane 3—3 of FIG. 2.

DETAILED DESCRIPTION

Typical apparatus 10 (FIG. 1) according to the present invention for obtaining fluorescence EXAFS data of a sample of material 11 comprises means such as a lens 12 for directing radiant energy 13 from a laser 14 onto a target 15 to produce X-rays 16 of a selected spectrum and intensity at the target 15, means such as a baffle 17 for directing X-rays 16 from the target 15 onto spectral-dispersive means such as a monochromator 18 located as to direct the spectrally-resolved X-rays 16R therefrom through a light-emitting grid 19 onto a sample of material 11, means such as the light-emitting grid 19 for absorbing the fluorescence X-rays emitted by the sample 11 and for emitting light 21 that is resolved spatially so as to correspond to the wavelength ($\lambda$) of the spectrally-resolved X-rays 16R striking the sample 11 and whose intensity at any point along the spatial light distribution corresponds to the intensity of said fluorescence X-rays 27 (FIG. 2) produced by a particular wavelength (80) of the incoming X-rays 16R, means such as an imaging lens 20 for directing the emitted light 21 produced by the fluorescence X-rays 27 from the light-emitting grid 19 onto a recording means such as a photographic film 22 so as to obtain a spectrum of the emitted light 21, and recording means such as a photographic film 29 (FIG. 2) for obtaining a reference spectrum of the spectrally-resolved X-rays 16R.

The radiant energy 13 typically comprises a laser pulse with a power density focused to at least about $10^{13}$ watts per square centimeter, and the target 15 typically comprises a solid (typically metal) surface, whereby a plasma is formed and raised to the kilovolt temperature regime. The laser pulse preferably is focused to strike a focal spot 23 on the target 15 about 10 to 1000 micrometers in diameter.

The X-rays from the target 15 preferably comprise continuum radiation in a selected EXAFS spectral regime of the sample 11. Typically the target 15 comprises essentially an element having a continuum just above the L-lines that includes a selected EXAFS spectral regime of the sample 11.

The means directing the X-rays from the target typically comprises a baffle 17 having an aperture 24 through which the X-rays 16 can proceed toward the spectral-dispersive means 18, which typically comprises a crystal monochromator. The spectral-dispersive means 18 typically comprises either a Bragg reflector or a diffraction grating, either flat (as in FIG. 1) or curved in any desired manner (not shown).

Typically the fluorescence X-ray absorbing means (light-emitting grid) 19 comprises an array of long, thin, equally-spaced, parallel, rectangular elements 25 arranged so that the narrow edge is esentially perpendicular to the incoming X-rays 16R. This permits the spectrally-resolved X-rays 16R to pass between the elements 25 and enter the sample of material 11 as shown in FIGS. 2 and 3. The rectangular elements 25 are about 1–10 mils apart on center and may be composed of a metal such as nickel and the like, a plastic, or a mixture of a plastic such as epoxy and a light-emitting material. The ratio of the width W of the channels 28 to the width W' of the rectangular elements 25 is preferably about 1:1 to 5:1.

As shown in FIG. 3, the sides of the rectangular elements 25 are coated with a light-emitting means such as a phosphor 26. Alternatively, the light-emitting material 26 may be incorporated throughout the elements 25 by forming them from a mixture of epoxy and phosphor particles (not shown). In either case, the surface of the elements 25 and any light-emitting material such as the phosphor 26 that is exposed to the incoming X-rays is coated with a material 30 such as nickel, copper, and the like that is opaque to X-rays. After the spectrally-resolved X-rays 16R enter the sample 11, they are reemitted from the sample 11 as fluorescence X-rays 27 that are essentially isotropic in angular distribution. Preferably for a sample such as aluminum, about 25 percent or more of the incoming X-rays 16R are reemitted as fluorescence X-rays 27. A portion (preferably about 25 percent or more) of the fluorescence X-rays 27 are absorbed in the phosphor 26 which then reemits them as light 21.

Each rectangular channel 28 defined by a pair of rectangular elements 25 is positioned in the path of the incoming spectrally-resolved X-rays 16R so that each rectangular channel 28 permits passage of only a narrow energy band of spectrally-resolved X-rays 16R. As a result, the spatial distribution of the rectangular channels 28 corresponds to the spectral distribution of the incoming X-rays 16R.

As shown in FIG. 3, the phosphor 26 can be shielded from the incoming X-rays 16R by a slight slanting of the sides of the rectangular elements 25 away from the incoming X-rays 16R.

The light emission of the phosphor 26 depends almost entirely on the number of fluorescence X-rays 27 incident on the phosphor 26. Therefore, it is important to have as many fluorescence X-rays as possible strike the phosphor coating 26. Preferably about 25 percent or more of the fluorescence X-rays should enter the phosphor 26. To achieve this entry rate, the ratio of the depth D of the channels 28 to the width W of the channels 28 should be about 2:1 to 10:1 and preferably at least about 4:1.

The emitted light 21 from the phosphor 26 is imaged onto a recording means through the use of about a one to one, fast (about f/$\frac{1}{2}$), relay lens 20. The recording means 22 can be either photographic film or an array detector such as the Reticon monolithic self-scanning linear silicon photodiode array manufactured by EG&G Reticon of Sunnyvale, CA. For film, the following reduction factors may be used to determine the exposure on the film from a single laser burst.

1. X-rays 16R passing into channel 28: 0.75
2. Fluorescence yield for Aluminum sample 11: 0.038
3. Fluorescence X-rays 27 captured by phosphor 26: 0.25
4. Phosphor efficiency: 0.25
5. Efficiency of 1:1 f/1.3 relay lens 20: 0.018

For an X-ray energy fluence of 10 ergs/cm$^2$, the expected light intensity on the film 22 is about $3.2 \times 10^{-4}$ ergs/cm$^2$. An ASA 20,000 film should give an optical density of 0.3 over fog.

Several factors enter into the selection of the phosphors 26. The most important is phosphor efficiency, that is, the percentage of fluorescence X-rays 27 that are captured by the phosphor 26 and emitted as light 21. Preferably this percentage should be about 25 percent or more. Secondly, the emission spectrum of the phosphor 26 should correspond to the optical characteristics of the recording means 22. Thus for film, it is desirable to have the optical spectral peak in the blue. For silicon detectors, a significant shift to the red is preferred. Of less importance are the decay time and particle size of the phosphors 26. Usually the decay time should be less than the response time of the recording means. With photographic film 22 as the detector, the decay time of the phosphor 26 is almost of no significance since the time required to remove the film is much longer than the usual decay time. However, with an array detector, it is advantageous to scan as rapidly as possible to minimize noise and therefore a short decay time is advantageous. Particle size is important only if the phosphor coating 26 is applied by a dip process. The few micron film thickness of the phosphor necessary to absorb the soft fluorescence X-rays can be sputtered or vacuum evaporated onto the grid. Some applicable common light-emitting materials are given below. This list is representative and not limiting. Other light-emitting materials and scintillators also are suitable for use with this invention.

| Phosphor | Color | Particle Size (microns) | Decay Time (seconds) | RETMA Designation Code |
| --- | --- | --- | --- | --- |
| $Zn_2SiO_4:Mn$ | Yellow-Green | 2–5 | $1.1 \times 10^{-2}$ | P1 |
| ZnS:Ag | White | Medium-Short Hyperbolic | | P4 |
| ZnCdS:Ag | | | | |
| ZnS:Ag, Ni | Blue | | Short, Hyperbolic | P11 |
| (ZnCd)S:Ag | Yellow-Green | Wide Range | Medium-Short Hyperbolic | P20 |
| ZnCdS:Cu, Ag | Green | 25 | Long, Hyperbolic | P28 |
| ZnS:Cu, Ag | Yellow-Green | 20 | Medium, Hyperbolic | P2 |
| $AlO_2Y_2:Ce$ | Green | 5 | Short | P46 |
| $CaWO_4$ | Blue | 3–5 | $1.1 \times 10^{-5}$ | P5 |
| $MgWO_4$ | Green | | | |
| $C_6H_4(CH)_2C_6H_4$ (anthracene) | Violet | | | |

In order to minimize the absorption of incoming X-rays 16R on the light-emitting grid 19 and maximize the X-rays 16R passing through it, it consists of an array of elements 25 such that the ratio of the width W of the channels 28 defined by the elements 25 to the width W' of the elements 25 is about 1:1 to 5:1.

The comparatively soft X-rays emitted by a low atomic number diluent of the sample 11 can be eliminated substantially by placing a thin filter such as a Mylar film (not shown) between the sample 11 and the fluorescence X-ray absorbing material 27. For diluents of substantially higher atomic number that produce L or M shell fluorescence, a filter comprising a material of the same atomic number as or an atomic number one less than the interfering diluent can be used.

The sample 11 can be in a variety of forms such as a powder or liquid. For samples such as liquids and powders, it is desirable to mount the light-emitting grid 19 in a horizontal position immediately above the surface of the sample so as to avoid any effects of an intervening container.

In FIG. 2, a reference spectrum of the incoming X-rays 16R is obtained by placing a recording means (detector) 29 immediately below the light-emitting grid 19 so that both the grid 19 and the detector 29 are both in the path of the incoming X-rays 16R. The detector 29 is not limited to a position immediately below the grid 29 but may be placed at any point along the path of the incoming X-rays 16R so long as it is positioned so that it is in the path of only a portion of the X-rays throughout the spectrum of the incoming X-rays 16R and the other portion of the X-rays throughout the spectrum is allowed to pass to the sample.

Alternatively, the reference-spectrum recorder may be substituted for the sample 11 and the light-emitting grid 19, in which case, the sample spectrum and the reference spectrum are obtained with separate pulses of radiant energy 13 from the laser 14. Typically, the recording means 29 for the reference spectrum comprises photographic film or an array detector.

A number of refinements of many of the aspects of this invention as well as an illustration of the techniques used in the evaluation of the spectral results obtained by using laser EXAFS have been discussed in our previous patent, U.S. Pat. No. 4,317,994; Mallozzi, et al., Mar. 2, 1982, all of which is hereby incorporated by reference. Techniques for evaluating spectral results using sample and reference spectra taken in different portions of the electromagnetic spectrum are well known and are discussed in *EXAFS Spectroscopy, Techniques and Applications*, Teo, B. K. and Joy, D. C, Editors, Plenum Press, New York, N.Y., 1981; which is also hereby incorporated by reference.

APPLICABILITY

Laser EXAFS spectroscopy is a powerful tool for obtaining chemical structural information such as the net charge on atoms and detailed information about the atomic environment of the X-ray absorbing atom including the distinction among nearest neighbors such as oxygen, nitrogen, sulfur, or carbon. Because of the short duration of the laser pulse, it is also possible to obtain structural information about short-lived intermediates and highly transient species. By combining laser EXAFS with a fluorescence X-ray detection system, it is possible to improve substantially the signal to noise ratio and thereby provide a technique capable of obtaining these types of structural information on atoms in very low concentrations, such as magnesium in chlorophyll, iron in blood, and atoms such as phosphorus, sulfur, chlorine, potassium, and calcium in other biological compounds of interest.

The combination of laser EXAFS and fluorescence X-ray detection also allows the use of sample forms that do not meet the exacting requirements of thinness and uniformity called for by conventional laser EXAFS. The more relaxed sample criteria of this invention allow for the use of the EXAFS technique on such diverse sample forms as liquids and powders.

Because of the far less rigid sample requirements, this invention allows laser EXAFS to be extended advantageously to routine laboratory and industrial applications.

While the forms of the invention herein disclosed constitute presently preferred embodiments, many others as possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. Apparatus for obtaining EXAFS data of a material, comprising:
   means for directing radiant energy from a laser onto a target in such manner as to produce X-rays at said target of a selected spectrum and intensity suitable for obtaining a fluorescence EXAFS spectrum of a material;

means for directing said X-rays from the target onto spectral-dispersive means so located as to direct spectrally-resolved X-rays therefrom onto a sample of material;

means for absorbing fluorescence X-rays emitted from said sample of material and for emitting light that is resolved spatially so as to correspond to the wavelength of the spectrally-resolved X-rays striking said sample and whose intensity at any point along the spatial light distribution corresponds to the intensity of said fluorescence X-rays produced by a particular wavelength of said incoming X-rays;

means for directing said emitted light onto recording means so as to obtain a spectrum of the emitted light; and means for obtaining a reference spectrum of said spectrally-resolved X-rays.

2. Apparatus as in claim 1, wherein said absorbing and emitting means comprises an array of elements arranged to permit said incoming X-rays to pass between said elements and enter into said sample of material.

3. Apparatus as in claim 2, wherein said array comprises an assembly of rectangular, equally spaced, parallel elements arranged such that the narrow edge of each element is essentially perpendicular to said incoming X-rays and said assembly is positioned such that the spatial distribution of the channels defined by each pair of elements corresponds to the spectral distribution of said incoming X-rays.

4. Apparatus as in claim 3, wherein said narrow edge of each element comprises a material opaque to X-rays.

5. Apparatus as in claim 4, wherein said opaque material comprises nickel or copper.

6. Apparatus as in claim 3, wherein said elements comprise essentially a metal, a plastic, or a mixture of plastic and light-emitting material.

7. Apparatus as in claim 3, wherein said elements comprise essentially nickel.

8. Apparatus as in claim 3, wherein said elements comprise a mixture of essentially epoxy and a light-emitting material.

9. Apparatus as in claim 3, wherein the ratio of the width of said channels defined by said elements to the width of said elements is about 1:1 to 5:1.

10. Apparatus as in claim 3, wherein the ratio of the depth of said channel to the width of said channel is about 2:1 to 10:1.

11. Apparatus as in claim 3, wherein side surfaces of said elements comprise material that emits light after absorbing said fluorescence X-rays emitted from said sample of material.

12. Apparatus as in claim 11, wherein the sides of said elements are slanted away from the path of said incoming X-rays so as to shield said light-emitting materials on said sides of said elements from said incoming X-rays.

13. Apparatus as in claim 11, wherein said light-emitting material has an optical spectral peak that corresponds to the optimal sensitivity of said recording means.

14. Apparatus as in claim 13, wherein said light-emitting material comprises a material that has said optical spectral peak in the blue and said recording means comprises photgraphic film.

15. Apparatus as in claim 13, wherein said light-emitting material comprises a material that has an optical spectral peak in the red and said recording means comprises a silicon photodiode array detector.

16. Apparatus as in claim 11, wherein said light-emitting material has a decay time less than the response time of said recording means.

17. Apparatus as in claim 11, wherein said light-emitting material comprises $Zn_2SiO_4$:Mn; ZnS:Ag; ZnCdS:Ag; ZnS:Ag,Ni; (ZnCd)S:Ag; ZnCdS:Cu,Ag; ZnS:Cu,Ag; $AlO_2Y_2$:Ce; $CaWO_4$; $MgWO_4$; anthracene ($C_6H_4(CH)_2C_6H_4$); or other scintillator.

18. Apparatus as in claim 1, wherein said emitted light-directing means comprises a fast relay lens.

19. Apparatus as in claim 1, wherein said recording means comprises photographic film.

20. Apparatus as in claim 1, wherein said recording means comprises an array detector.

21. Apparatus as in claim 1, wherein said means for obtaining said reference spectrum comprises photographic film placed in the path of said spectrally-resolved X-rays so as to record said reference spectrum and said spectrum of said emitted light with a single pulse of said radiant energy from said laser.

22. Apparatus as in claim 1, wherein said means for obtaining said reference spectrum comprises an array detector placed in the path of said spectrally-resolved X-rays so as to record said reference spectrum and said spectrum of said emitted light with a single pulse of said radiant energy from said laser.

23. Apparatus as in claim 1, wherein said reference spectrum and said spectrum of said emitted light are obtained by using separate pulses of said radiant energy from said laser.

24. Apparatus as in claim 1, wherein a filter is placed between said sample and said fluorescence X-ray absorbing means so as to filter out unwanted radiation.

25. Apparatus as in claim 24, wherein said filter comprises a Mylar film so as to filter out soft X-rays emitted by low atomic number diluents.

26. Apparatus as in claim 24, wherein said filter comprises a material of the same atomic number as or an atomic number one less than a diluent that produces L or M shell fluorescence.

27. Apparatus as in claim 1, wherein said sample comprises a powdered material.

28. Apparatus as in claim 1, wherein said sample comprises a liquid.

* * * * *